(12) United States Patent
Gang et al.

(10) Patent No.: US 11,866,775 B2
(45) Date of Patent: Jan. 9, 2024

(54) METHODS FOR ISOTHERMAL MOLECULAR AMPLIFICATION WITH NANOPARTICLE-BASED REACTIONS

(71) Applicant: Brookhaven Science Associates, LLC, Upton, NY (US)

(72) Inventors: Oleg Gang, Setauket, NY (US); Suchetan Pal, New York, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 491 days.

(21) Appl. No.: 17/065,255

(22) Filed: Oct. 7, 2020

(65) Prior Publication Data

US 2021/0024990 A1 Jan. 28, 2021

Related U.S. Application Data

(62) Division of application No. 15/983,804, filed on May 18, 2018, now abandoned.

(60) Provisional application No. 62/508,682, filed on May 19, 2017.

(51) Int. Cl.
| | | |
|---|---|---|
| *C12Q 1/6862* | (2018.01) | |
| *B82Y 5/00* | (2011.01) | |
| *C12Q 1/6853* | (2018.01) | |
| *C12Q 1/6844* | (2018.01) | |

(52) U.S. Cl.
CPC .............. *C12Q 1/6862* (2013.01); *B82Y 5/00* (2013.01); *C12Q 1/6844* (2013.01); *C12Q 1/6853* (2013.01); *C12Q 2545/101* (2013.01)

(58) Field of Classification Search
CPC .. C12Q 1/6862; C12Q 1/6844; C12Q 1/6853; C12Q 1/682; C12Q 2545/101; C12Q 2563/149; C12Q 2563/155; B82Y 5/00
See application file for complete search history.

(56) References Cited

U.S. PATENT DOCUMENTS 11,513,076 B2 * 11/2022 Grabmayr .......... G01N 21/6428

OTHER PUBLICATIONS

Zhang et al. A DNA-origami chip platform for label-free SNP genotyping using toehold-mediate strand displacement. Small (2010) vol. 6, No. 17, pp. 1854-1858. (Year: 2010).*
Zhu et al. Toehold-mediated strand displacement reaction triggered isothermal DNA amplification for highly sensitive and selective fluorescent detection of single-base mutation. Biosensors and Bioelectronics (2014) 59:276-281. (Year: 2014).*
Dirks et al. Triggered amplification by hybridization chain reaction. Proc. Natl. Acad. Sci. (2004) vol. 101, No. 43, pp. 15275-15278. (Year: 2004).*

* cited by examiner

*Primary Examiner* — David C Thomas
(74) *Attorney, Agent, or Firm* — Dorene Price

(57) ABSTRACT

The present method of detection involves increasing an amount of analyte molecules by an isothermal molecular amplification approach. In the present approach a starting molecule of interest may be amplified through a reaction it induces with specifically engineered and functionalized particles, namely protected particles A and storage particles B. This reaction may result in a set of output DNA molecules that is larger in number than the input DNA molecules. Thus the reaction between nanoparticles for amplification of a certain DNA sequence (input DNA molecules) may occur when there is a match with a targeted molecule (stored molecules on storage particles B) and if the DNA sequence of the input DNA molecules does not match (partially or completely) the targeted molecule the reaction may not occur. Without a certain molecular input of the input DNA molecule the reaction may not occur.

18 Claims, 7 Drawing Sheets
(7 of 7 Drawing Sheet(s) Filed in Color)
Specification includes a Sequence Listing.

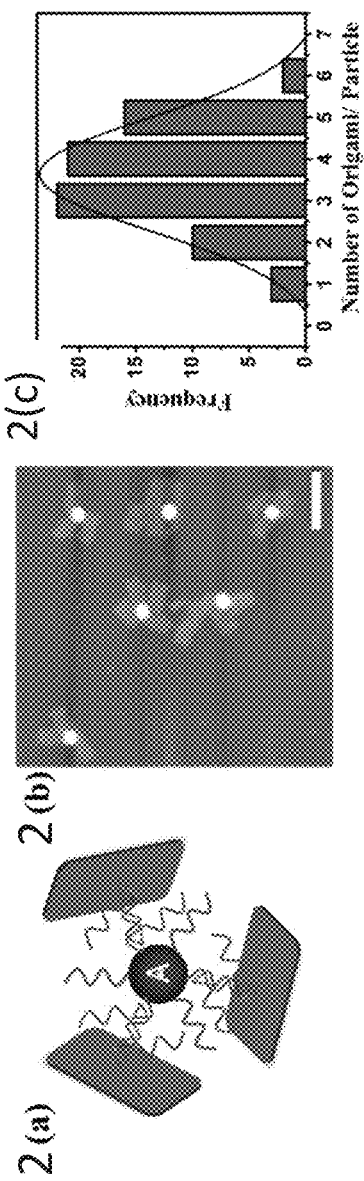
Fig. 2(a)(b)(c)

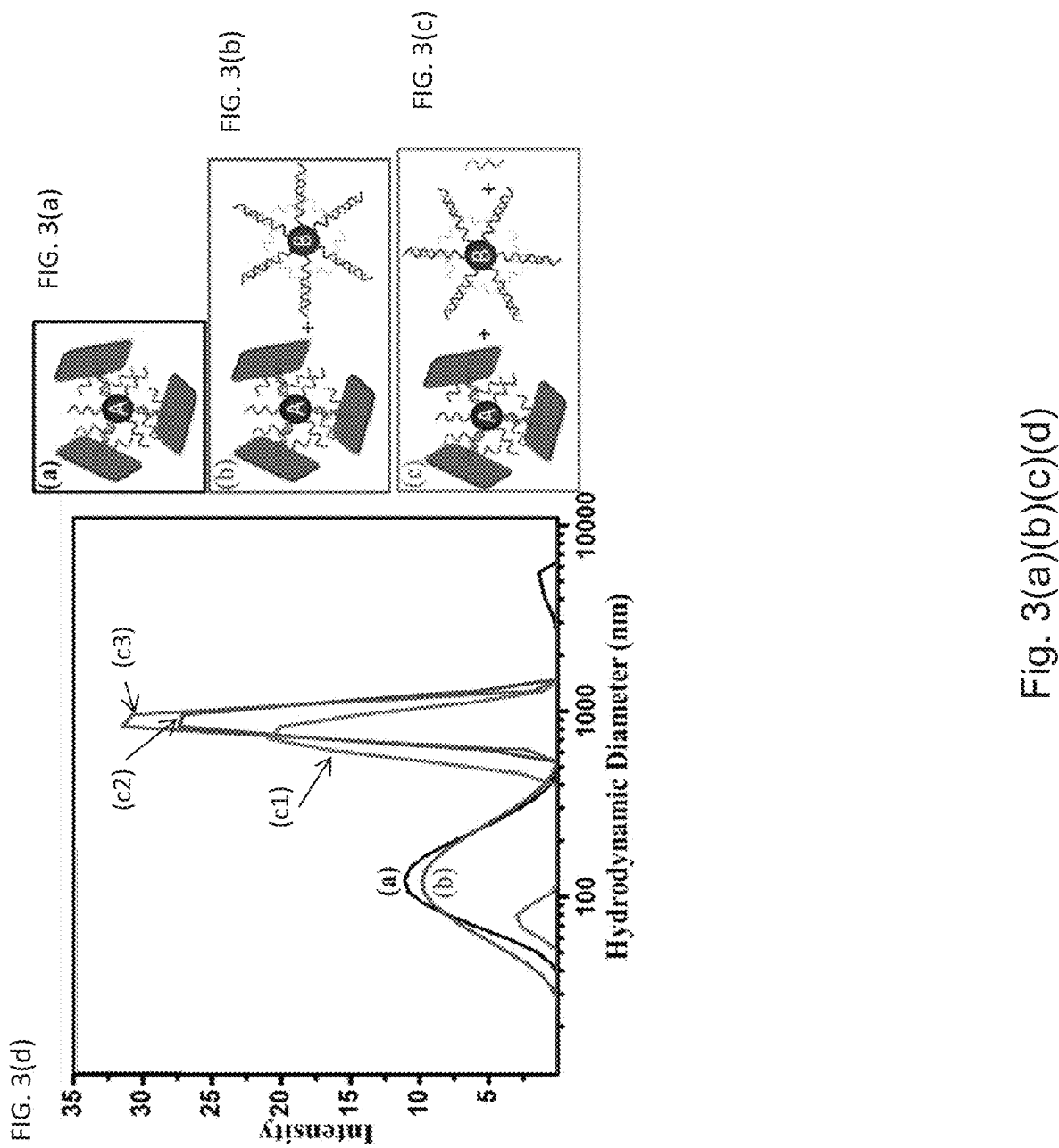
Fig. 3(a)(b)(c)(d)

SEQUENCE LISTING

```
<160> NUMBER OF SEQ ID NOS: 4

<210> SEQ ID NO 1
<211> LENGTH: 10
<212> TYPE: DNA
<213> ORGANISM: Artificial Sequence
<220> FEATURE:
<223> OTHER INFORMATION: DNA Fragment

<400> SEQUENCE: 1
aatcgcatgc                                                          10

<210> SEQ ID NO 2
<211> LENGTH: 10
<212> TYPE: DNA
<213> ORGANISM: Artificial Sequence
<220> FEATURE:
<223> OTHER INFORMATION: DNA Fragment

<400> SEQUENCE: 2
```

```
gcatgcgatt                                                              10

<210> SEQ ID NO 3
<211> LENGTH: 10
<212> TYPE: DNA
<213> ORGANISM: Artificial Sequence
<220> FEATURE:
<223> OTHER INFORMATION: DNA Fragment

<400> SEQUENCE: 3
gctgctgtaa                                                              10

<210> SEQ ID NO 4
<211> LENGTH: 10
<212> TYPE: DNA
<213> ORGANISM: Artificial Sequence
<220> FEATURE:
<223> OTHER INFORMATION: DNA Fragment

<400> SEQUENCE: 4
ttacagcagc                                                              10
```

METHODS FOR ISOTHERMAL MOLECULAR AMPLIFICATION WITH NANOPARTICLE-BASED REACTIONS

CROSS-RELATED APPLICATION

The present application is a divisional application of U.S. application Ser. No. 15/983,804, filed on May 18, 2018, which claims priority from U.S. Provisional Application No. 62/508,682, filed May 19, 2017, each of which is incorporated herein by reference in their entirety.

STATEMENT OF GOVERNMENT RIGHTS

The present application was made with government support under contract number DE-SC0012704 awarded by the U.S. Department of Energy. The United States government has certain rights in the invention(s).

FIELD OF THE INVENTION

This application relates to isothermal molecular amplification with nanoparticle-based reactions.

BACKGROUND OF THE INVENTION

Bio-sensing, counterfeit detection and chemical safety require sensitive detection of minute amounts of target molecules. That is, such detection requires complex and costly methods to reveal infinitesimal amounts of materials. In some cases, single molecule level detection may be achieved through optical methods. However challenges may remain for use of such optical methods for practical real-life applications. Other methods of detection may use physical detection such as, for example, fluorescent detection, Raman signal, plasmonic shift or the like.

State of the art physical detection methods focus on the detection side of molecular sensing, i.e. they are based on enhancing the sensitivity of the detection apparatus or applying methods that permit more sensitive detection modes/principles. However, there is still a need to address the other side of the detection process by increasing the incoming molecular signal.

SUMMARY OF THE INVENTION

The present isothermal molecular amplification approach relates to a method of detection by increasing an amount of analyte molecules. In the present approach a starting molecule of interest (e.g., DNA with specific input sequence as the analyte molecule or referred to also as an input DNA molecule (yellow)) may be amplified through a reaction it induces with specifically engineered and functionalized particles, namely protected particles A and storage particles B. This reaction may result in a set of output DNA molecules (yellow) that is larger in number than the input DNA molecules (yellow).

The reaction between nanoparticles for amplification of a certain DNA sequence (input DNA molecules (yellow)) may occur when there is a match with a targeted molecule (stored molecules (yellow)) on storage particles B, and if the DNA sequence of the input DNA molecules (yellow) does not match the targeted molecule the reaction may not occur. Without a certain molecular input of the input DNA molecule (yellow) the reaction may not occur.

The amplification by this reaction may be by a factor of about 100-500, and larger factors may be achieved through optimization and system design that one skilled in the art may carry out. The present isothermal molecular amplification system may be utilized with known detection methods, thus, it may enhance the sensitivity of other methods.

A sensor apparatus for detecting targeted molecules comprising one or more protected particles A, storage particles B and input DNA molecules wherein protected particles A comprise first sequence (red) strands and second sequence (green) strands functionalized thereon, storage particles B comprise third sequence (purple) strands grafted thereon and stored targeted DNA molecule (yellow) partially hybridized thereon, protected particles A, deprotected by input DNA molecules, react with storage particles B by a duplex between third sequence (purple) strands and first sequence (red strands), and wherein input DNA molecules have a matching DNA sequence with stored targeted DNA (yellow) molecules and output DNA molecules (yellow).

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The patent or application file contains at least one drawing executed in color. Copies of this patent or patent application publication with color drawing(s) will be provided by the Office upon request and payment of the necessary fee.

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 2(a) shows schematic representation of origami protected particle A;

FIG. 2(b) AFM topography of the construct respectively. The scale bar is 200 nm;

FIG. 2(c) shows a histogram of the number of origami attached to the 20 nm AuNP A (bar) and a Gaussian function fitting (line curve) to the number distribution, on average there are approximately 3-4 origami attached to each DNA coated AuNP A;

FIG. 3(a) is a schematic representation of origami protected particle A;

FIG. 3(b) is a schematic representation of origami protected particle A and storage particle B;

FIG. 3(c) is a schematic representation of origami protected particle A, storage particle B and input DNA molecule (yellow strand);

FIG. 3(d) DLS hydrodynamic diameter of construct of system shown in FIGS. 3(a)-(c): origami protected particles A (FIG. 3(a)) shown by curve labeled (a); origami protected particles A and storage particles B (FIG. 3(b)) mixed but not activated by input DNA molecule (yellow strand) shown by curve labeled (b); origami protected particles A, storage particles B with added input DNA molecule (yellow strand) (FIG. 3(c)) added in different concentrations—10 nM shown by curve labeled (c1), 100 nM shown by curve labeled (c2), and 1000 nM shown by curve labeled (c3) respectively;

FIG. 4(b) shows a schematic representation and a change of fluorescence with a 1:1 ratio of protected particles A and storage particles B (2.1 nM each), and 0.5 nM of input DNA molecules (yellow strands) combined together;

FIG. 4(d) shows the kinetics of the present amplification reaction, monitored by in situ fluorescence and DLS measurements; the reaction is completed within 1 hour of initiation;

DETAILED DESCRIPTION OF THE INVENTION

Figure 1A:
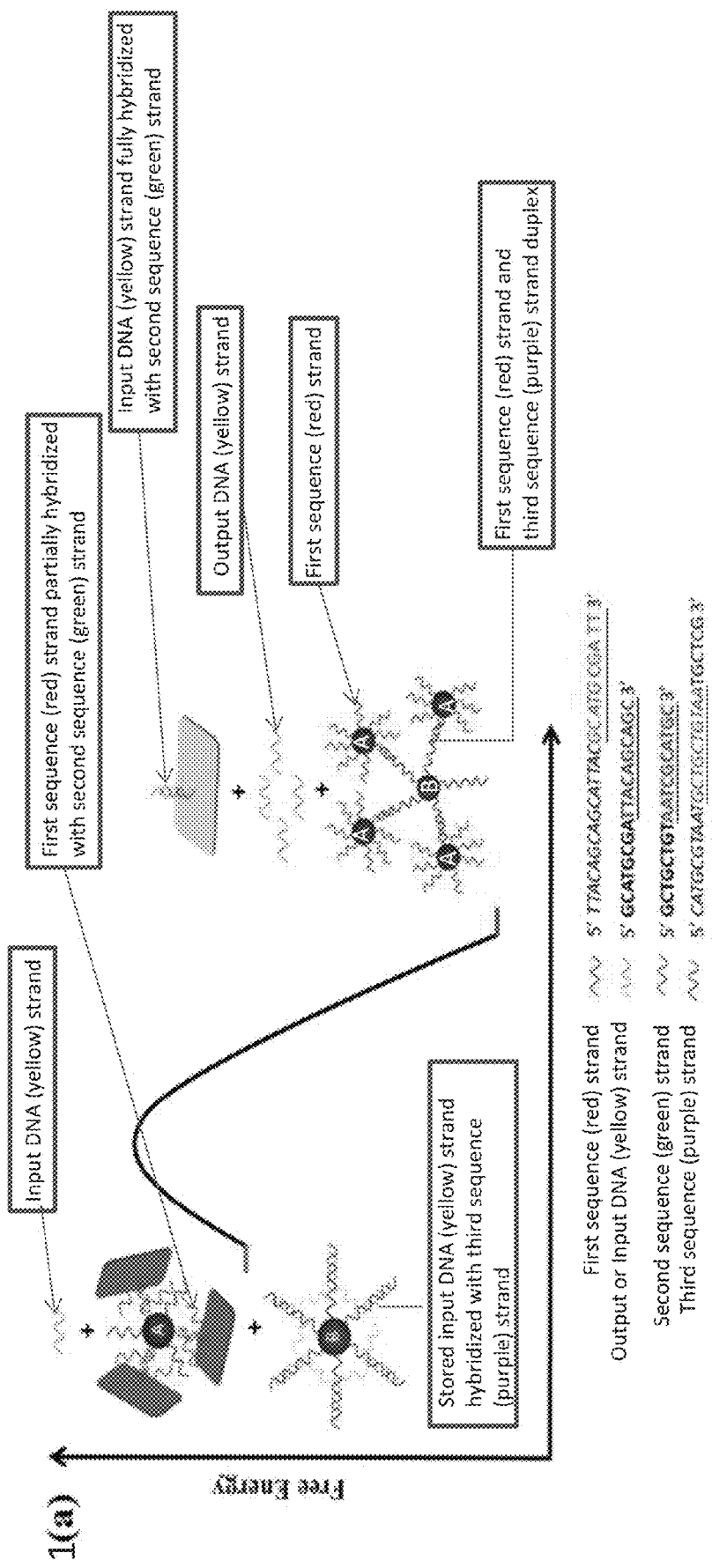
FIG. 1(a) shows an energy landscape of present isothermal DNA amplification and illustration of an example of an overall scheme of an isothermal molecular amplification reaction system.

In the following Detailed Description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

It will be understood that any compound, material or substance which is expressly or implicitly disclosed in the specification and/or recited in a claim as belonging to a group or structurally, compositionally and/or functionally related compounds, materials or substances, includes individual representatives of the group and all combinations thereof.

The present oligonucleotides can be any type of oligonucleotide, either naturally-occurring or artificial. Typically, the oligonucleotide is DNA or RNA.

In one embodiment, an isothermal molecular amplification approach is provided by which a molecule of interest (e.g., DNA with a specific sequence as an analyte molecule, or referred to also as an input oligonucleotide molecule (yellow) or "Input-Oligonucleotide") may be amplified to produce output molecules (i.e., "Stored-Input-Oligonucleotide") with the same or different oligonucleotide (e.g., DNA) sequence through a reaction that may be induced between specifically designed and oligonucleotide functionalized particles, namely protected particles A (i.e., "Particle-A") and storage particles B (i.e., "Particle-B"). As a result, more output oligonucleotide molecules (yellow), of the same sequence as the input molecules (yellow), may be produced than the input oligonucleotide molecules (yellow) originally added. The molecule of interest may be a targeted or analyte input DNA molecule and may be designated as yellow strands. The input molecule may be a single stranded oligonucleotide (e.g., DNA) sequence, e.g., DNA with a length of between about 10 to 120 bases. Input DNA molecules (yellow) may be added to initial or partially deprotected particles A. A mixture of protected particles A comprising oligonucleotide origami and storage particles B can be prepared, formulated and/or provided.

Initial or Deprotected Particles a (i.e., Deprotected "Particle-A")

Initial or deprotected nanoparticles or particles A may be functionalized with first sequence oligonucleotide (e.g., DNA) strands and second sequence oligonucleotide (e.g., DNA) strands. First sequence and second sequence strands may be complementary in sequence to one another. The first sequence strand may be designated as red strands (or "Oligonucleotide-1") and the second sequence strand may be designated as green strands (or "Oligonucleotide-2"). Thus, second sequence strand (green strands) may be complementary in sequence with first sequence strands (red strands.) First sequence strands and second sequence strands (i.e., green and red strands) may partially hybridize to form "Duplex 1-2". Typically, Oligonucleotide-1 is grafted to Particle-A.

Partially hybridized first sequence strands and second sequence strands green and red strands) may facilitate binding of oligonucleotide (e.g., DNA) origami to initial or deprotected particles A. Oligonucleotide origami may protect initial or deprotected particles A from reacting to form aggregates or binding with targeted particles B. When oligonucleotide origami binds to initial or deprotected particles A they are transformed to protected particles A.

Protected Particles A (i.e., Protected "Particle-A")

The design of protected nanoparticles or particles A may render them nonreactive and protected from aggregation with other particles, namely storage particles B (i.e., "Particle-B"). The design of protected particles A may be rendered reactive with the addition of an input oligonucleotide molecule (yellow). The protected particle A when reacted with the input oligonucleotide molecule (yellow) (i.e., "Oligonucleotide-Y") may become partially or fully deprotected and amplification may be enabled. The amplification reaction may proceed until the deprotected particles A are consumed/reacted and no more release is possible (i.e., substantially all or all stored input oligonucleotide molecules are released and the reaction ends). Fully deprotected particles A cannot bind to input oligonucleotide molecule (yellow).

The protected particles A may have a shell or a shield of oligonucleotide origami. Oligonucleotide origami may act as a protective shield ("umbrella" or "blocking plates") for initial or deprotected designed particles A transforming them to protected particles A. Blocking plates may comprise oligonucleotide (e.g., DNA) origami. Oligonucleotide origami may be bound to initial or deprotected designed particles A. In some embodiments, oligonucleotide origami may be planar and have a shape that is rectangular, round or other designed 2-dimensional constructs, or may be a 3-dimensional construct, such as, for example, polyhedron shaped. Planar oligonucleotide origami plates may be bound to initial designed nanoparticles or deprotected particles A may act as a protective shield/shell ("umbrella" or "blocking plates"). The oligonucleotide origami may be a coating on particles A.

Oligonucleotide origami may provide steric shielding against hybridization between oligonucleotide strands (e.g., first sequence (red) strands, i.e., "Oligonucleotide-1") bound to particles A and oligonucleotide strands bound to other particles (e.g., storage particles B). Specifically, oligonucleotide origami may provide steric shielding against hybridization of third sequence (purple or "Oligonucleotide-3") strands on storage particles B and first sequence (red or "Oligonucleotide-1") strands on initial or deprotected particles A. Such a design of the shell may prevent aggregation of particles A with, for example, storage particles B in the solution when no input DNA molecule (yellow or "Input-Oligonucleotide") is present. The oligonucleotide origami shape can be designed by one skilled in the art to maximize the particle A shielding or optimize other reaction parameters (e.g. DNA hybridization with input DNA).

Storage Particles B (i.e., "Particle-B")

Storage nanoparticles or particles B (i.e., Particle-B) may be functionalized with third sequence strands. The third sequence strands may be grafted onto storage particles B. The third sequence strands may be designated as purple strands (or "Oligonucleotide-3"). Third sequence (purple) strands may form a duplex with first sequence (red) strands of initial or deprotected particles A, i.e., when particles A are not protected by oligonucleotide origami. Such duplex is referred to as "Duplex 1-3." Storage particles B may also have stored input DNA molecules, designated as yellow strands hybridized partially on them, e.g., a hybridization between "Oligonucleotide-3" and "Stored-Input-Oligonucleotide" to form "Duplex 3-Y." Stored input oligonucleotide molecules (yellow) partially hybridized on storage particles B may have the same or different oligonucleotide sequence as input oligonucleotide molecule (yellow). If it is a different sequence, then there may be a portion or part that is different and a portion or part that is the same. For example, less than about 50%, about 40%, about 30%, about 20, about 10% or about 5% can be different.

Amplification Reaction

The reaction between specifically engineered and oligonucleotide-functionalized nanoparticles, namely partially deprotected particles A (i.e., "Particle-A") and storage particles B (i.e., "Particle-B"), may result in amplification of a certain oligonucleotide (e.g., DNA) sequence of stored input DNA molecules (yellow) on storage particles B if they match a targeted or analyte input DNA molecule (yellow) and a cascade reaction is induced. On the other hand, if the oligonucleotide sequence of stored input DNA molecules on storage particles B do not match the targeted input oligonucleotide molecule, no reaction may take place. No reaction may occur without addition of a targeted or analyte input DNA molecule to partially deprotected particles A and storage particles B.

An input oligonucleotide molecule (yellow) (e.g., a single stranded DNA sequence, "Input-Oligonucleotide") may induce an amplification reaction between certain designed initial or partially deprotected particles A ("Particle-A") and storage particles B ("Particle-B"). The reaction may produce and result in a release of new output DNA molecules (yellow) stored on storage particles B ("Stored-Input-Oligonucleotide"). When input oligonucleotide molecules (yellow) are added to protected particles A, the protected particles A may be deprotected. When protected particles A are partially deprotected, an amplification or cascade reaction may produce output oligonucleotide molecules (yellow) in a much larger number/amount than the input oligonucleotide molecules (yellow) that were added to start the reaction. In turn, the released new output DNA molecules may act as input DNA molecule and promote one or more follow-on (second, third, and so on) reaction(s) and new additional output DNA molecules (species) of the same sequence (T1) or different sequence (T2) may be produced and released. The cascade reaction may repeat until protected particles A are fully deprotected.

As used herein amplification refers to a number of output oligonucleotide (e.g., DNA) molecules that is larger than input oligonucleotide molecules. The amplification by the present reaction may be by a factor of 100-200, 100-300, 100-400, or 100-500 and larger factors depending on the details of the desired nanoparticle design, i.e. it size, sequence length, environmental parameters etc. The amplification factor (i.e., ratio of output number of molecules to input number of molecules) may depend on the size of nanoparticles A and B (about 10-20 nm), design of the shell and protection shield (DNA origami), and reaction parameters (e.g., salt, particle concentration, DNA, temperature). The amplification reaction may occur without temperature ramping. The operational temperature for the "amplifier" may be determined by nanoparticle design, as would be known to a skilled artisan, so it may be referred to as an isothermal amplification. The operational temperature may be room temperature.

The input molecules (yellow) are capable of deprotecting a subset of the protected particles A partially by removing one or more 'umbrella' oligonucleotide (e.g., DNA) origamis ("blocking plates"). The protected particles A may be deprotected by release of blocking plates. After particles A are deprotected, a duplex between third sequence (purple) strands on particles B and first sequence (red) strands on particles A may be energetically favorable (i.e., "Duplex 1-3"). Deprotected particles A and storage particles B may bind when first sequence (red) and third sequence (purple) strands are able to hybridize. Multiple binding of particles A and B may result in particle aggregation rather than isothermal amplification.

For example, after adding 0.5 nM input DNA (yellow) molecules, the reaction between partially deprotected particles A and storage particles B (having stored input (yellow) strands partially hybridized on it) may be activated. Stored input DNA (yellow) strands on storage particles B may be hybridized with third sequence (purple) strands that are grafted on. The inter-particle reaction between partially deprotected particles A and storage particles B may produce and release new output molecules (yellow) of the same or different type (that have been stored on the particles B). In turn, the newly released output oligonucleotide molecules (yellow) may further promote inter-particle reaction that may lead to further releases of output oligonucleotide molecules (yellow). Thus, amplification of the input DNA molecules (yellow) in the cascade of "chain"-like reactions may be obtained. (The amount of input DNA molecule (yellow) may be, for example, about 0.5 nM to about 1000 nM.)

As depicted in FIG. 1(a), the energy landscape of the present isothermal oligonucleotide molecule amplification system may relate to a transition from a higher energy metastable state to a lesser energy configuration to a lowest energy state. This transformation through the energy states from a high energy state to low energy state may be via a sequential toehold mediated strand displacement reaction by input oligonucleotide molecule (yellow). The input oligonucleotide molecules (strands) may be utilized to overcome an initial energy barrier, or may be utilized to activate the amplification reaction through for example, deprotection (i.e., release) of blocking plates, made out of oligonucleotide origami.

In one embodiment, input molecules and output molecules may be the same and amplification of the same type (noted as 'T1') may occur. The amplification reaction may be activated through deprotection (i.e., release of blocking plates made out of oligonucleotide origami) of particles A and the reaction may feed itself: additional strands of output molecules may be released while A and B particles begin to aggregate due to binding of oligonucleotide on their surfaces. The reaction may end when substantially all or all initial particles A are reacted and output molecules (the same type as the input molecule, but larger amount than the input molecules) are released.

In one embodiment, multiplication of other predefined molecules may be achieved, whereby an input molecule 'T1' may result in the release of output molecules 'T2' (stored on storage particles B), and the amount of 'T2' may be larger than 'T1'. The amplification factor may be defined as a ratio of the number/concentration of output molecules to the number/concentration of input molecules, i.e. [T2]/[T1].

Another Embodiment

In one embodiment, a method for amplifying an Input-Oligonucleotide is provided. The Input-Oligonucleotide can be of any length. Typically, the Input-Oligonucleotide is about 5 to about 200 bases, or about 10 to about 120 bases. Typically, the Input-Oligonucleotide is an unknown sample of oligonucleotides that is to be identified.

The method includes the use of a plurality of particles. The particles can be any type of particle to which oligonucleotides can be grafted. Typically, the particles can have diameters in the nanometer to micron range. For example, nanoparticle can range from about 5 to about 100 nm in diameter. Typically, the particles are metallic or semiconducting. Examples of suitable particles include gold (Au), silver (Ag), copper (Cu), platinum (Pt), palladium (Pd) and combinations thereof. A plurality of such particles is functionalized with oligonucleotides. Particles which are functionalized with the same oligonucleotides have the same designation.

For example, a plurality of particles, designated as Particle-A, can be functionalized with a plurality of Oligonucleotide-1 and a plurality of Oligonucleotide-2. Typically, Oligonucleotide-1 is grafted onto Particle-A. There are about 25 to about 400 Oligonucleotide-1 attached per about 5 nm to about 40 nm diameter of Particle-A. Typically, there are about 200 Oligonucleotide-1 attached per about 20 nm diameter of Particle-A. Oligonucleotide-1 is hybridized to Oligonucleotide-2 to form Duplex 1-2. Typically, Duplex 1-2 is formed by a partial hybridization.

Oligonucleotide origami is attached to Duplex 1-2 to render Particle-A non-reactive (i.e., protected). The origami can be any size which protects Particle-A. The origami is 2-dimensional or 3-dimensional, for example, the origami can be rectangular. A typical size of the origami is about 5 to about 100 nm per about 20 nm of particle diameter, for example, about 50 nm in length per about 20 nm diameter of Particle-A. Due to selective hybridization between Oligonucleotide-1 and Oligonucleotide-2, Particle-A may bind to several origami structures. Typically, there can be about 2 to about 10 origami per about 5 nm to about 40 nm diameter of Particle-A. For example, there can be about 3 to about 4 origami per about 20 nm diameter of Particle-A.

Additionally, a plurality of particles, designated as Particle-B, can be functionalized with a plurality of Oligonucleotide-3 and a plurality of Stored-Input-Oligonucleotide. Typically, Oligonucleotide-3 is grafted onto Particle-B. Typically, there are about 25 to about 400 Oligonucleotide-3 attached per about 5 nm to about 40 nm diameter of Particle-B. For example, there can be about 200 Oligonucleotide-3 attached per about 20 nm diameter of Particle-B. Oligonucleotide-3 is hybridized to Stored-Input-Oligonucleotide to form Duplex 3-Y. Typically, Duplex 3-Y is formed by a partial hybridization. Typically, the hybridization does not take place at the ends of the oligonucleotide strands; that is, hybridization takes places within the strands, referred to as "inter-strand" hybridization.

In one embodiment, at least a portion of the sequences of Input-Oligonucleotide and the Stored-Input-Oligonucleotide are identical. For example, the sequences are at least about 50%, about 60%, about 70%, about 80%, about 90%, about 95%, about 97%, about 98%, about 99% or 100% identical.

The Input-Oligonucleotide, Particle-A and Particle-B are mixed. The mixing can occur in any order. Typically, the reaction is under isothermal conditions. For example, the whole reaction can occur at about room temperature. Typically, the relative amount of Particle-A:Particle-B is about 10:1 to about 1:10, e.g., about 1:1. Typically, the relative amount of Input-Oligonucleotide to Particle-A is at least about 1:4. The amount of Input-Oligonucleotide to Particle-A can be in vast excess, e.g., about 1000:4

Typically, the Input-Oligonucleotide is added to Particle-A first. Once mixed, a cascade reaction occurs so that: i) the Input-Oligonucleotide hybridizes with Oligonucleotide-2 to form Duplex Y-2, thereby removing Oligonucleotide-2 and origami from Particle-A, and exposing Oligonucleotide-1, ii) exposed Oligonucleotide-1 hybridizes with Oligonucleotide-3 to form Duplex 1-3, thereby releasing Stored-Input-Oligonucleotide, and iii) step (i) reoccurs with the Stored-Input-Oligonucleotide replacing the Input-Oligonucleotide until the reaction terminates. Typically the reaction terminates because the Stored-Input-Oligonucleotide has all been released. By the reaction, the Input-Oligonucleotide is amplified by the release of the Stored-Input-Oligonucleotide. Typically, the Input-Oligonucleotide is amplified by a factor of about 50 to about 1000.

The reaction can occur efficiently because the melting temperature (Tm) of Duplex Y-2 is greater than the Tm of Duplex 1-2; and the Tm of Duplex 1-3 is greater than the Tm of Duplex 3-Y. For example, the Tm of Duplex Y-2 is at least about 5% greater or at least about 20% greater than the Tm of Duplex 1-2. The Tm of Duplex 1-3 is at least about 5% greater or at least about 20% greater than the Tm of Duplex 3-Y.

In another embodiment, a method for identifying an Analyte-Oligonucleotide is provided. The method comprises providing a plurality of Particle-A and a plurality of Particle-B. Particle-A is functionalized with Oligonucleotide-1 and Oligonucleotide-2. Oligonucleotide-1 and Oligonucleotide-2 are hybridized to form Duplex 1-2, and have attached oligonucleotide origami. The origami renders Particle-A non-reactive. Oligonucleotide-1 is typically grafted onto Particle-A. Particle-B is functionalized with Oligonucleotide-3 and Target-Oligonucleotide. Typically, Oligonucleotide-3 is grafted onto Particle-B. Oligonucleotide-3 and Target-Oligonucleotide are partially hybridized to form Duplex 3-Y. The Analyte-Oligonucleotide, Particle-A and Particle-B are mixed, in any order. If the sequences of the Analyte-Oligonucleotide and the Target-Oligonucleotide are substantially identical (e.g. 99% or 100% identical), a cascade reaction occurs so that: i) the Analyte-Oligonucleotide fully hybridizes with Oligonucleotide-2 to form Duplex Y-2, thereby removing Oligonucleotide-2 and origami from Particle-A, and exposing Oligonucleotide-1, ii) exposed Oligonucleotide-1 partially hybridizes with Oligonucleotide-3 to form Duplex 1-3, thereby releasing Target-Oligonucleotide, and iii) step (i) reoccurs with the Target-Oligonucleotide replacing the Analyte-Oligonucleotide. The Analyte-Oligonucleotide is identified as being the Target-Oligonucleotide if Particle-A and Particle-B aggregate in the reaction mixture.

In another embodiment, a sensor apparatus for identifying an Analyte-Oligonucleotide is provided. The apparatus comprises a plurality of Particle-A, and a plurality of Particle-B. Particle-A is functionalized with Oligonucleotide-1 and Oligonucleotide-2. Oligonucleotide-1 and Oligonucleotide-2 are hybridized to form Duplex 1-2. Oligonucleotide Origami is attached to Duplex 1-2. The origami renders Particle-A non-reactive. Oligonucleotide-1 is typically grafted onto Particle-A. Particle-B is functionalized with Oligonucleotide-3 and Target-Oligonucleotide. Typically, Oligonucleotide-3 is grafted onto Particle-B. Oligonucleotide-3 and Target-Oligonucleotide are hybridized to form Duplex 3-Y. An Analyte-Oligonucleotide is mixed with Particle-A and Particle-B, in any order. If at least a portion of the sequence of Analyte-Oligonucleotide is identical to the Target-Oligonucleotide, a cascade reaction occurs so that: i) the Analyte-Oligonucleotide fully hybridizes with Oligonucleotide-2 to form Duplex Y-2, thereby removing Oligonucleotide-2 and origami from Particle-A, and exposing Oligonucleotide-1, ii) exposed Oligonucleotide-1 partially hybridizes with Oligonucleotide-3 to form Duplex 1-3, thereby releasing Target-Oligonucleotide, and iii) step (i) reoccurs with the Target-Oligonucleotide replacing the Analyte-Oligonucleotide. The Analyte-Oligonucleotide is identified as being the Target-Oligonucleotide if there is an aggregation of Particle-A and Particle-B in the reaction mixture.

EXAMPLES

Example 1

Figure 1B:
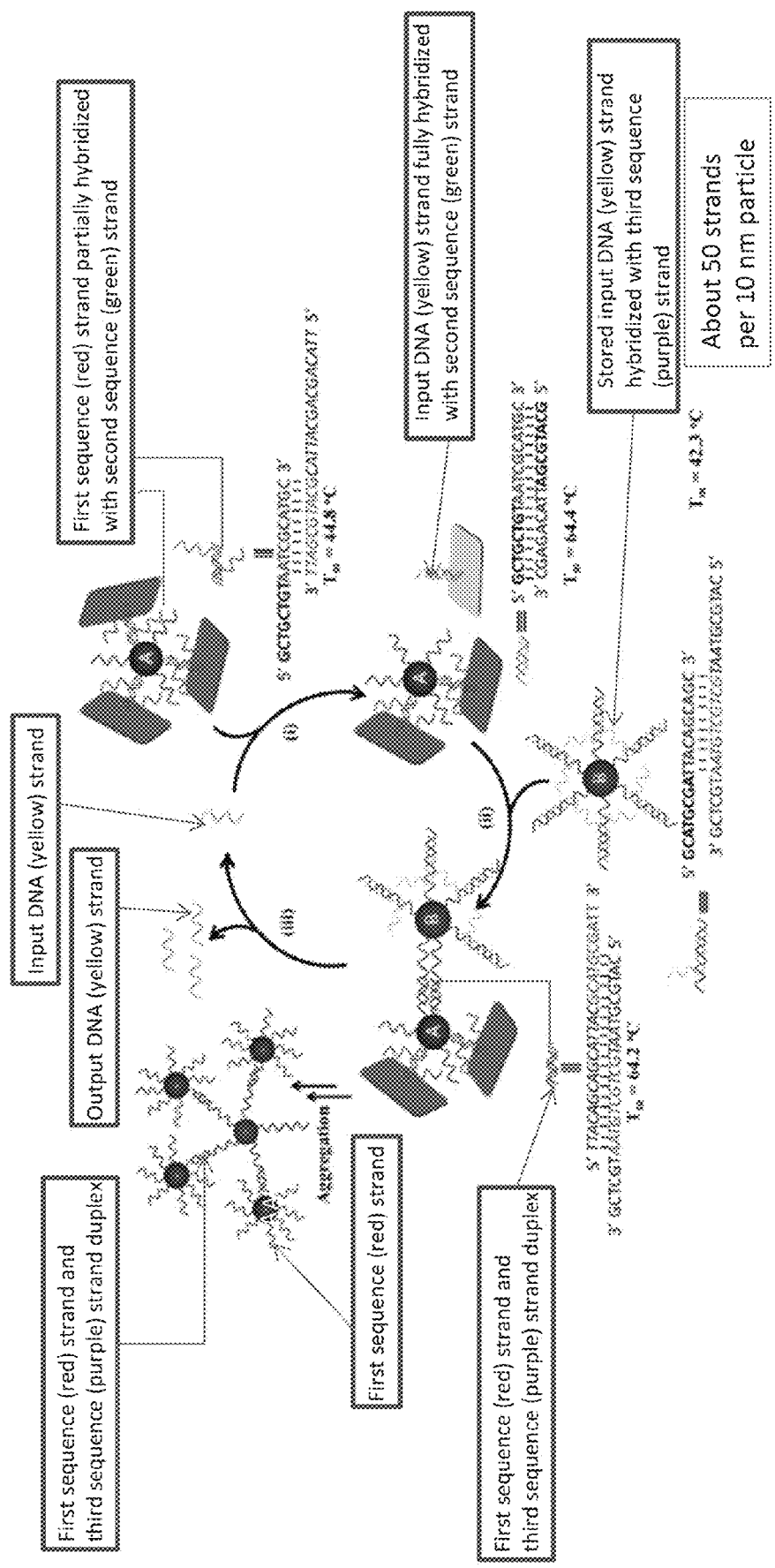
FIG. 1(b) shows DNA replacement reaction induced aggregation and isothermal amplification of yellow DNA molecule (about 50 strands per 10 nm particle)

Begin with two 20 nm gold nanoparticles (AuNP), namely AuNP A (initial or deprotected particles A) and AuNP B (storage particles B), where each may be functionalized with '(red strand)' first sequence strands and '(purple strand)' third sequence strands of DNA, respectively. Red (first sequence) strands may be grafted on AuNP A and purple (third sequence) strands may be grafted on AuNP B. There may be an approximately 200 first sequence (red) strands on AuNP A and approximately 200 third sequence (purple) strands on AuNP B. AuNP A, in addition to the first sequence (red) strand, may be functionalized with a second sequence (green) strand. Part of the second sequence (green strand) of DNA may contain a sequence portion (5' AAT CGC ATG C 3'—underlined) which may be complementary to the part of first sequence (red) strand of DNA sequence (5' GCA TGC GAT T 3'—underlined). First sequence and second sequence (green and red) strands of AuNP A may be partially hybridized. Due to selective hybridization between the first sequence and second sequence (red and green) strands particle (AuNP) A may bind to several origami structures as shown in FIG. 1(b)(i). Particle (AuNP) A may be protected by the origami structures.

On the other hand, in FIG. 1(a), AuNP B functionalized with the third sequence (purple) strand, has a part of the third sequence 'purple strand' that may contain a sequence (5' GCT GCT GTA A 3'—underlined) which may be complementary to a part of a yellow (input) strand of DNA sequence (5' TTA CAG CAG C 3'—underlined) of an input molecule. The yellow (input) strand may have a specific inter strand hybridization with the third sequence (purple) strand. The specific inter strand hybridization may allow input molecule (yellow) to bind to storage particle (AuNP) B as shown in FIG. 1(b)(ii).

DNA replacement reaction induced aggregation and isothermal amplification of DNA input molecule (yellow input strand) is shown in FIG. 1(b). First, in FIG. 1(b)(i), input DNA molecule (yellow strand) may fully hybridize with second sequence (green) strand (Tm~64.4° C.) of particle (AuNP) A (initial or protected particle). Partially hybridized second sequence and first sequence (green and red) strands (Tm~44.8° C.) may be displaced. This displacement may lead to deprotection of first sequence (red) strands grafted on now deprotected particle (AuNP) A (former initial or protected particles). The origami structures bound to initial or protected particle (AuNP) A may be released. First sequence (red) strands of deprotected particle (AuNP) A may be exposed.

The exposure of first sequence (red) strands of partially deprotected particle (AuNP) A may lead to a further DNA replacement induced aggregation reaction as shown in FIG. 1(b)(ii). At this point, partially complementary stored input molecule (yellow strand) and third sequence (purple) strands (Tm~42.3° C.) on storage particle (AuNP) B may be displaced by partially deprotected AuNP A and exposed first sequence (red) strands on partially deprotected particle (AuNP) A forming a first sequence (red) and third sequence (purple) strand duplex (Tm~64.2° C.). Subsequent release of multiple output molecules (yellow strands) and aggregation of partially deprotected particles (AuNPs) A and storage particles B may occur as shown in FIG. 1(b)(iii).

The formation of the duplex between third sequence (purple) strands and first sequence (red) strands may be energetically favorable and if these two strands are able to hybridize then partially deprotected particles A and storage particles B may bind (i.e., aggregate). Multiple binding of particles A and particles B may result in particle aggregation rather than isothermal amplification. Bare particles A and particles B functionalized with first sequence (red) strands and third sequence (purple) strands respectively may aggregate upon mixing at room temperature as first sequence (red) and third sequence (purple) strands may hybridize with each other.

Input molecules (yellow (input) strands) of DNA may be added in an amount of 0.5 nM to the solution containing origami protected or initial particles A and stored input molecules (yellow strands) hybridized with third sequence (purple) strands grafted on particle B. The amount of stored input molecules (yellow strands) may be 0.5 nM to 1000 nM. A 0.5 nM or greater amount of yellow (input) strands may lead to a cascade of reactions and may produce and release a larger number of output molecules of DNA (yellow strands) than input strands (yellow) as delineated in FIG. 1(b).

As shown in FIG. 1(a), there may be a higher energy of hybridization between input DNA molecules (yellow) strands and second sequence (green) strands on protected particles A as compared to second sequence (green) strands and first sequence (red) strands. Selective hybridization between second sequence (green) strands and first sequence (red) strands on some protected particles A may be interrupted. One or more of the DNA origami bound to protected particles A may be ejected from particles A. The removal of DNA origami from protected particles A or from the vicinity of protected particle A may lead to the activation of several first sequence (red) strands on deprotected particle A which were previously dormant when under the protected particles A that had "umbrella" shielding of the DNA origami.

As shown in FIG. 1(b)(ii), the activated first sequence (red) strands on partially deprotected particle A may hybridize with third sequence (purple) strands of storage particle B. Stored input molecules (yellow strands) from storage particles B in the solution may be released. As shown in FIG. 1(b)(iii), released output molecules (yellow strands) may in turn release more DNA origami shields on remaining protected particles A, and that may promote a cascade of deprotection and hybridization events between partially deprotected particles A and storage particles B. The outcome of the avalanche may be a liberation of output molecules of single-stranded (ss) yellow output strands triggered by a small amount of input molecules (yellow strands) thereby achieving an amplification of the input molecule (yellow strand). The cascade reaction may be irreversible.

Example 2—Fabrication and Characterization of AuNP-Origami Constructs (Protected Particles A)

AuNP-Origami constructs were fabricated by mixing 20 nm AuNPs A and rectangular origami together (several per particle) by mixing and letting origami hybridize on initial or deprotected particles A.

After purification by known methods such as for example gel electrophoresis, atomic force microscopy (AFM) measurements were carried out to characterize origami-AuNP conjugates (protected particles A). An AFM image is shown in FIG. 2(b). The height profile extracted from AFM imaging shows several DNA origami structures with approximately 1.5 nm height that are connected to an approximately 18 nm height spherical AuNP (particles A) in high yield. There are very few unbound DNA origami found in the area of view suggesting serial purification was successful. In FIG. 2(c) a histogram of number of origami bound to one particle A is shown and the distribution fits a Gaussian profile. On an average 3-4 origami structures were found to be connected to one 20 nm AuNP A. The hydrodynamic diameter of the construct was measured to be 200 nm with broad size distribution using Dynamic Light Scattering (DLS) shown as black trace in FIG. 3(d) which is significantly larger than that of only origami (70 nm) and the AuNP A (30 nm). Amplification experiments were conducted with these as prepared AuNPs with AuNP-origami constructs (protected particles A).

Amplification Experiments:

An experiment was conducted in a test tube at room temperature by mixing particles (AuNPs) A protected with origami (protected AuNP-A) with storage particles B having stored input (yellow) strands on it (AuNP-B-Y). Particles A and B are in a 1:1 ratio, where Y represents third sequence (purple) strands hybridized with stored input (yellow) strands on storage particle B. The concentration (amount) is 2.1 nM each of particle A and particle B. The outcomes of the experiments were verified by two methods, DLS measurements and steady state fluorescence spectroscopy. These inter-particle hybridization reactions were completed within one hour as shown in FIG. 4(c), as verified by in situ fluorescence and DLS measurements.

DLS (Dynamic Light Scattering) Measurements.

The ensemble hydrodynamic diameter was measured of a 1:1 mixture with protected particle A (protected AuNP-A) and storage particle B having stored input (yellow) strands on it (AuNP-B-Y) [where Y denotes third sequence (purple) strand hybridized with stored (yellow) strands on storage particle B where stored (yellow) strands have the same or different DNA as yellow input strands]. The concentration is 2.1 nM for each of protected particle A and storage particle B and is shown by trace (b) in FIG. 3(d). The ensemble hydrodynamic diameter exhibited similar size distribution for only protected AuNP A size distribution except there is a shoulder at lower size due to the presence of smaller AuNP-B-Y (hydrodynamic diameter approximately 30 nm). The ensemble hydrodynamic diameter did not change over time for up to several hours validating a premise of steric protection of protected particle A from reaction with storage particle B (i.e., protected particles A were protected against aggregation).

To the approximately 2 nM solution of each protected particle A and storage particle B, different amounts of input molecules (yellow strands) were added and kept at room temperature for 12 hours. Addition of 1 (1000 nM) input molecule (yellow strand) was found to lead to aggregation of aggregates of partially deprotected particles A with storage particles B with sizes shown by trace (c3) in FIG. 3(d). The amount of input molecule (yellow strand) was sequentially decreased by orders of magnitude and found that 100 nM (trace (c2)) and 10 nM (trace (c1)) concentration of input molecule (yellow strands) leads to aggregations of partially deprotected particles A with storage particles B as shown by and trace respectively. The concentration of input molecule (yellow strand) decreased to 0.5 nM was found to lead to visible aggregation of partially deprotected particles A with storage particles B. However, the system without any input molecule (yellow strand) added remained dispersed without signs of aggregations between protected particles A with storage particles B. Thus, the DLS measurements showed that the presence of 0.5 nM amount of yellow input strand (which can be considered miniscule) leads to a cascade of strand displacement reactions, which, in turn, leads to aggregation of partially deprotected particles A and storage particles B, and the release of output molecules (yellow strands) greater than input molecules (yellow strands) i.e. amplification of input molecules (yellow strands). In order to gain a quantitative picture of this amplification process, a fluorescence enhancement assay described in the following section was developed.

Fluorescence Measurements:

In order to obtain a quantitative understanding of the number of output molecule (yellow DNA strands) released during the aggregation of partially deprotected particles A and storage particles B, Cy5 labeled yellow DNA was used.

Cy5 has excitation maximum at approximately 650 nm and emission maximum at approximately 670 nm. The metal nanoparticle surface is in close proximity to the bound fluorophores and typically exhibits a quenched fluorescence. However, when the fluorophores are displaced from the metal surface proximity, the fluorescence is recovered back to the intrinsic fluorescence value. This method was used to quantify the amount of output molecules (yellow DNA strands) released from the cascade reaction. The number of stored input molecules (yellow strands) carried by storage particle B was estimated. Known 500 times excess of fluorophore modified yellow input strand was added to a known concentration in nanomolar range depending on particular analysis of storage particle B, for example, in the 1 to 10 nM range. Although 500 times of Cy5-yellow DNA (Cy5) was added, it was found that approximately 200 times remained in the solution as estimated by UV-Vis and fluorescence measurements of the supernatant. These results indicated that there are approximately 300 copies of stored input molecules (yellow DNA strands) on a single storage particle B. To figure out the quenching effect of 20 nm AuNPs on the Cy5, a strand displacement assay was carried out. Different amounts of excess of first sequence (red) strands on partially deprotected particles A, which is fully complementary to the input molecules (yellow input strands) were added to the AuNP-Y-Cy5 (labeled storage particle B) solution.

Figure 4A:
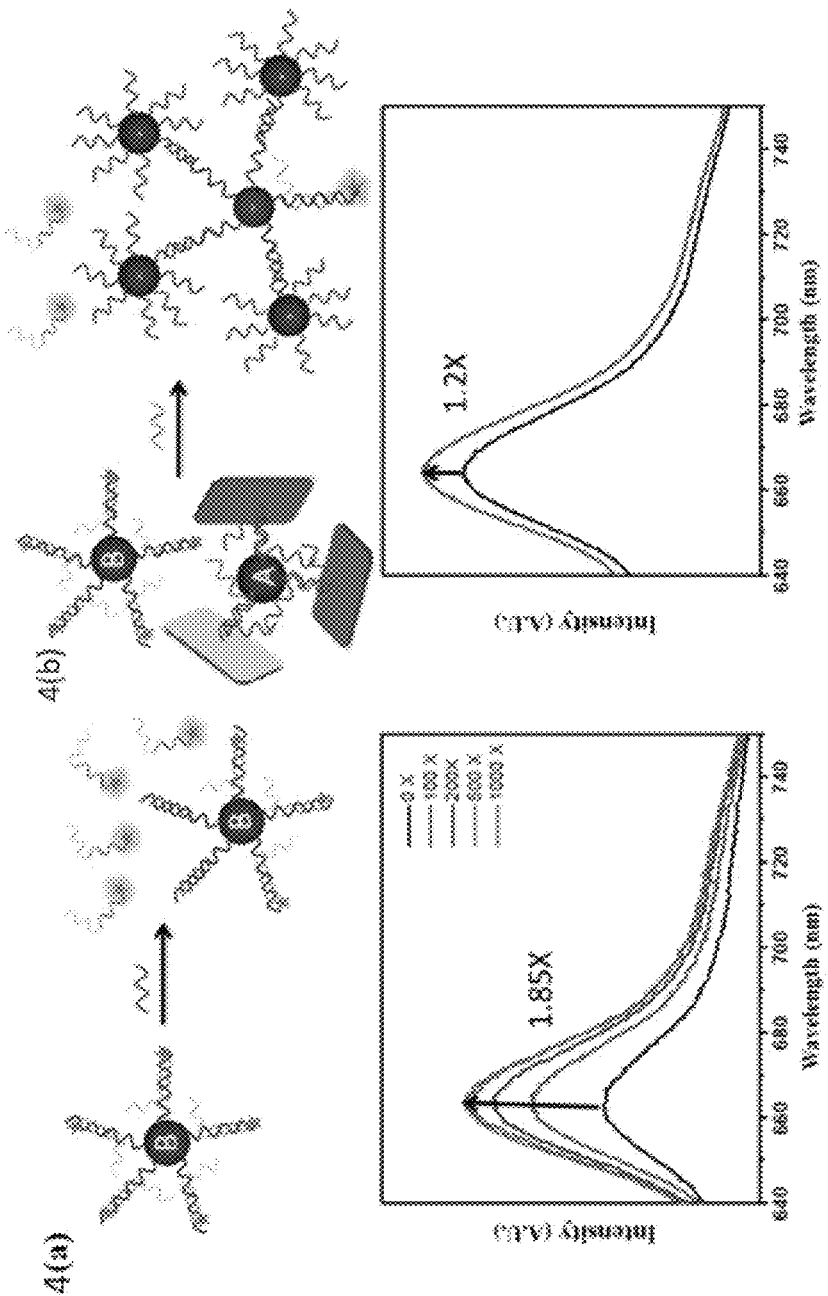
FIG. 4(a) shows a schematic representation and a change of fluorescence of storage particle B (2.1 nM) with the addition of excess of first sequence (red) DNA strand.
Figure 4C:
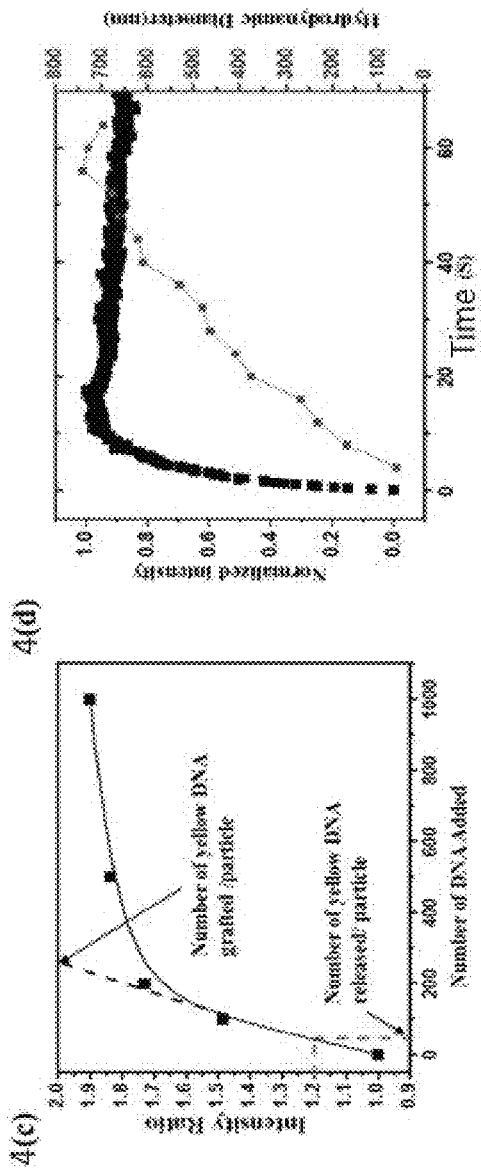
FIG. 4(c) relative change of fluorescence intensity with increasing amount of first sequence (red) DNA strand added shown as black squares. The x-axis intercept line is a straight black dotted line labeled as the number of yellow DNA grafted/particle and corresponds to the number of stored input molecules (yellow DNA strands) on storage particles B. The change in the intensity for the fluorescence enhancement assay experiments for origami protected particles A and storage particles B-Y-Cy5 is approximately 1.2 (portion of dotted line parallel to x axis and labeled "Number of yellow DNA released/particle") corresponds to 40-50 output DNA molecules (yellow strands) released per particle (portion of dotted line parallel toy axis and labeled "Number of yellow DNA released/particle")

FIGS. 4(a) through (d) show results from a fluorescence enhancement assay for the determination of the number of DNA released. Due to high thermodynamic stabilization of duplex formation between first sequence (red) and third sequence (purple) strands, excess first sequence (red) strands can chase off input molecule (yellow strands) in the solution creating a separation between the fluorophore and AuNP shown in the upper panel of FIG. 4(a). The change in steady state fluorescence change is shown in FIG. 4(a). In the presence of 300 times excess yellow input strands it is observed that the fluorescence signal of Cy5 gets amplified by approximately 1.85 times the initial intensity. In FIG. 4(c), the relative fluorescence intensity change is plotted with the increasing amount of the first sequence (red) DNA strand added. The plot shows steady increase of the fluorescence up to 200 times excess of first sequence (red) DNA strands. As first sequence (red) DNA amount increases no change of intensity was observed, and this suggests that the bound yellow-Cy5 DNA input strands were removed by the excess of first sequence (red) DNA strands. The intercept of the black dotted line with x-axis in FIG. 4(c), corresponds to the number of stored input molecule (yellow DNA) per particle. This observation further verifies that there are approximately 300 stored input molecules (yellow DNA input strands) grafted on storage particle B.

Fluorescence enhancement assay was carried out to investigate how many yellow-Cy5 strands were released during the aggregation of partially deprotected particles A and storage particles B in the absence or presence of 0.5 nM input molecules (yellow DNA strands). During the aggregation process involving AuNPs A and B, all of the complementary DNAs are not necessarily fully hybridized. Thus, a certain percentage of output molecules (yellow strands) were released, as shown in the upper panel FIG. 4(b). The amount of the output molecules (yellow DNA strands) released could be estimated from the fluorescence signal change in the solution. The observed change was 1.2-1.4 times that of the initial intensity. The dotted lines in FIG. 4(c) indicate the number of released DNA, based on the fluorescence signal change. This result suggested that 15-22% of the yellow-Cy5 input strands were released from the storage particles B during the aggregation process. The amplification factor was calculated as a number of output molecules (yellow strands) released (output) per one input molecule (yellow input strand) as 200-300, as shown in Table 1.

TABLE 1

Amplification factor is the ratio of amount of output strand released to input strand (or a number of output strands per one input strand) for the experimental realizations.

| Conc. of Particle A (nM) | Conc. of Particle B (nM) | Conc. of Input DNA (nM) | ~Output DNA Released (nM) | Amplification Factor |
|---|---|---|---|---|
| 2.1 | 2.1 | 0.5 | 300*.15*2.1 | 191 |
| 2.1 | 2.1 | 0.5 | 300*.22*2.1 | 277 |

Molecular Selectivity for Amplification Reaction:

The robustness of the present molecular amplification approach in the presence of slightly different input molecules was investigated. This investigation tested the selectivity of amplification (i.e., only targeted or analyte input molecules are amplified) and how the system can withstand the interference from other non-targeted molecules. The point mutations in DNA can produce very similar molecular species and may not be distinguishable from the original DNA. These mutations may relate to the origin of genetic disorders or may be the cause for cancer. Robustness of amplification against sequence mutations may contribute counterfeit detection, chemical safety, bio-sensing, DNA nanotechnology, information-computing and other applications. Improved detection sensitivity of targeted molecules may be useful in bio-sensing, DNA nanotechnology, information-computing, counterfeit detection, chemical safety and other applications.

Figure 5:
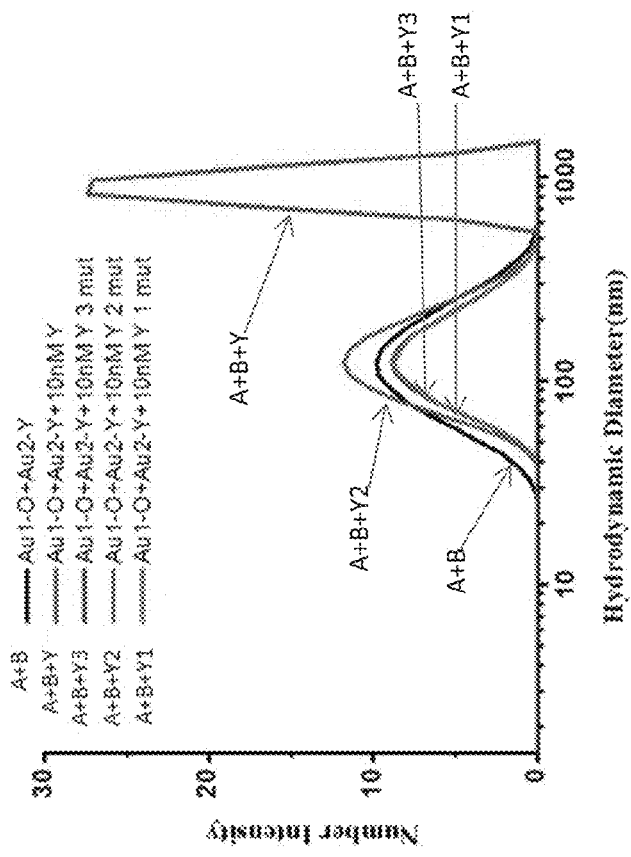
FIG. 5 shows the effect of DNA mutation on the aggregation. A+B represents a 1:1 ratio of origami protected particles A and storage particles B-Y-Cy5. A+B+Y represents when 10 nM of input DNA molecules (yellow) are added to a solution of A+B leading to an aggregation of A and B particles. Presence of 10 nM of input DNA molecules (yellow) with three mutations (A+B+Y3), two mutations (A+B+Y2) and one mutation (A+B+Y) failed to produce any aggregations; and all arranged according to at least some embodiments described herein.

The present amplification system was tested in the presence of the modified input molecules (yellow strands) with 1, 2 and 3 point mutations. The point mutations are replacement of a single base nucleotide with another randomly chosen base (from the other three bases). Three sequences were selected to mimic the 1, 2 and 3 point mutations shown in FIG. 5. At low concentrations of 10 nM, it was observed that the mutated input molecules (mutated yellow strands) are not able to initiate the cascade reaction, as evident from the absence of aggregations confirmed by no change in the DLS hydrodynamic diameter (FIG. 5). This experiment illustrates that the present amplification method is capable of discriminating the signal from closely related signals with near or at 100% specificity. Thus the present amplification system can be utilized with other intricate amplification schemes and circuits (analogues to electronics) that can perform complex operations with an input molecular signal for a variety of applications.

Additional Embodiments

In one embodiment, a method is provided for isothermal molecular amplification comprising formulating a mixture of protected particles A comprising DNA origami and of storage particles B, where protected particles A do not react with storage particles B, where storage particles B are hybridized with stored input DNA molecule (yellow) having an input sequence, and where stored input DNA molecule (yellow) has the same input sequence as or has a portion of input sequence that is the same as an input DNA molecule (yellow); adding the input molecule (yellow) to the mixture; releasing DNA origami from some of the protected particles A and deprotecting some of the protected particles A; iii. released origami reacting with input DNA molecule (yellow); deprotected particles A reacting with storage particles B and inducing release of stored input DNA molecule (yellow) from storage particle B as an output DNA molecule (yellow); and released output DNA molecule (yellow) mixing with some of the remaining protected particles A creating a cascade reaction of ii. through iv. repeating until stored input DNA molecules are released and deprotected particles A are fully deprotected. In one embodiment, protected particles A are functionalized with first sequence (red) strands and second sequence (green) strands. In one embodiment, protected particles A are functionalized with first sequence (red) strands and second sequence (green) strands that are complementary in sequence with one another. In one embodiment, partially hybridized first sequence (red) strands and second (green) strands permit binding of origami to protect particles A. In one embodiment, protected particles A are functionalized with first sequence (red) strands and second sequence (green) strands and wherein input molecule Y fully hybridizes with second sequence (green) strands. In one embodiment, partially hybridized first sequence (red) strands and second sequence (green) strands permit binding of origami to protect particle A, wherein input molecule (yellow) fully hybridizes with second sequence (green) strands and displaces partially hybridized first sequence (red) strands and second sequence (green) strands, and wherein origami is released, protected particles A are deprotected and first sequence (red) strands are exposed. In one embodiment, protected particles A are functionalized with first sequence (red) strands and second sequence (green) strands, and storage particles B are functionalized with third sequence (purple) strands, wherein deprotecting particle A exposes first sequence (red) strands, and wherein exposed first sequence (red) strands form a duplex with third sequence (purple) strands. In one embodiment, protected particles A are functionalized with first sequence (red) strands and second sequence (green) strands, and storage particles B are functionalized with third sequence (purple) strands, wherein deprotecting protected particles A exposes first sequence (red) strands, and wherein exposed first sequence (red) strands form a duplex with third sequence (purple) strands, and deprotected particles A bind with storage particles B. In one embodiment, storage particles B are functionalized with third sequence (purple) strands. In one embodiment, storage particles B are functionalized with third sequence (purple) strands, and third sequence (purple) strands form a duplex with first sequence (red) strands of deprotected particle A. In one embodiment, storage particles B are functionalized with third sequence (purple) strands and wherein third sequence (purple) strands are complementary in sequence with part of stored input molecule (yellow). In one embodiment, partially hybridized third sequence (purple) strands of storage particles B and stored input molecule Y permit binding of stored input molecule (yellow) to storage particle B. In one embodiment, the invention is a DNA output molecule produced by the aforementioned methods. In one embodiment, the present invention provides a sensor apparatus for detecting targeted molecules comprising one or more protected particles A, storage particles B and input DNA molecules wherein protected particles A comprise first sequence (red) strands and second sequence (green) strands functionalized thereon, storage particles B comprise third sequence (purple) strands grafted thereon and stored targeted DNA molecule (yellow) partially hybridized thereon, protected particles A, deprotected by input DNA molecules, react with storage particles B by a duplex between third sequence (purple) strands and first sequence (red strands), and input DNA molecules have a matching DNA sequence with stored targeted DNA (yellow) molecules and output DNA molecules (yellow).

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

INCORPORATION OF SEQUENCE LISTING

Incorporated herein by reference in its entirety is the Sequence Listing for the application. The Sequence Listing is disclosed on a computer-readable ASCII text file titled, "BSA17-02_IP2016-016-01_sequence_listing.txt", created on Aug. 7, 2018. The BSA17-02_IP2016-016-01_sequence_listing.txt file is 2 KB in size.

The invention claimed is:

1. A method for amplifying a molecular signal of an Input-Oligonucleotide, the method comprising
   a) providing a plurality of Particle-A protected by oligonucleotide origami, wherein Particle-A is functionalized with a plurality of Oligonucleotide-1, wherein a sequence in Oligonucleotide 1 complementary to a sequence in a plurality of Oligonucleotide 2 hybridize to form Duplex 1-2, and sequence in Oligonucleotide 2 complementary to a sequence in oligonucleotide origami hybridize;
   b) providing a plurality of Particle-B, wherein Particle-B is functionalized with a plurality of Oligonucleotide-3, wherein a sequence in Oligonucleotide-3 complementary to a sequence in a plurality of Stored-Input-Oligonucleotide hybridize to form Duplex 3-Y; and
   c) mixing the Input-Oligonucleotide, plurality of origami protected Particle-A and plurality of Particle-B, in any order, wherein a cascade reaction occurs so that:
   i) sequence in the Input-Oligonucleotide complementary to sequence in Oligonucleotide-2 hybridize to form Duplex Y-2, thereby removing Oligonucleotide-2 and the oligonucleotide origami, and exposing Oligonucleotide-1 on Particle A,
   ii) sequence in Oligonucleotide-1 complementary to sequence in Oligonucleotide-3 hybridize to form Duplex 1-3, thereby releasing the Stored-Input-Oligonucleotide hybridized to the sequence in Oligonucleotide-3,
   iii) sequence in the Stored-Input Oligonucleotide released in ii) complementary to sequence in Oligonucleotide-2 hybridize to form Duplex Y-2, thereby removing Oligonucleotide-2 and the oligonucleotide origami, and exposing Oligonucleotide-1 on Particle A to hybridize to complementary sequence in Oligonucleotide-3 to form Duplex 1-3, thereby releasing the Stored-Input-Oligonucleotide hybridized to the sequence in Oligonucleotide-3, and,
   iv) where (iii) reoccurs until the cascade reaction terminates, when Particle A are fully deprotected.

2. The method of claim 1, wherein the cascade reaction terminates by a first occurrence of either complete deprotection of origami protected Particle A or the release of all Stored-Input-Oligonucleotide from Duplex 3-Y.

3. The method of claim 1, wherein Duplex Y-2 has a Tm 20% greater than the Tm of Duplex 1-2.

4. The method of claim 1, wherein Duplex 1-3 has a Tm 20% greater than the Tm of Duplex 3-Y.

5. The method of claim 1, wherein the Input-Oligonucleotide is DNA or RNA.

6. The method of claim 1, wherein the Particle-A and the Particle-B are nanoparticles from about 5 to about 100 nm in diameter.

7. The method of claim 6, wherein the nanoparticles are selected from the group consisting of Au, Ag, Cu, Pt, Pd and combinations thereof.

8. The method of claim 1, wherein the Input-Oligonucleotide consists of about 5 to about 120 bases.

9. The method of claim 1, wherein there are about 25 to about 400 Oligonucleotide-1 attached per about 5 nm to about 40 nm diameter of Particle-A.

10. The method of claim 1, wherein there are about 25 to about 400 Oligonucleotide-3 attached per about 5 nm to about 40 nm diameter of Particle-B.

11. The method of claim 1, wherein the oligonucleotide origami is 2-dimensional or 3-dimensional.

12. The method of claim 1, wherein the oligonucleotide origami is rectangular, round or polyhedron.

13. The method of claim 1, wherein the oligonucleotide origami is rectangular.

14. The method of claim 1, wherein there are about 3 to about 4 origami per about 20 nm diameter of Particle-A.

15. The method of claim 1, wherein the cascade reaction is under isothermal conditions.

16. The method of claim 1, wherein the cascade reaction is under room temperature.

17. The method of claim 1, wherein the released Stored-Input-Oligonucleotide is measured.

18. The method of claim 17, wherein the amplified molecular signal of the released Stored-Input-Oligonucleotide is measured.

* * * * *